(12) United States Patent
Jiang et al.

(10) Patent No.: US 11,129,754 B2
(45) Date of Patent: Sep. 28, 2021

(54) METHOD FOR MANUFACTURING MEDICAL SPONGE FOR ORTHOPEDIC TREATMENT BY UNILATERAL PRESSING

(71) Applicant: WUXI SECOND PEOPLE'S HOSPITAL, Jiangsu (CN)

(72) Inventors: Yu Jiang, Jiangsu (CN); Zhaomin Zhong, Jiangsu (CN); Guoxing Zhu, Jiangsu (CN); Chenye Yuan, Jiangsu (CN); Lina Chen, Jiangsu (CN)

(73) Assignee: Wuxi Second People's Hospital, Wuxi (CN)

( * ) Notice: Subject to any disclaimer, the term of this patent is extended or adjusted under 35 U.S.C. 154(b) by 0 days.

(21) Appl. No.: 17/229,004

(22) Filed: Apr. 13, 2021

(65) Prior Publication Data
US 2021/0228421 A1    Jul. 29, 2021

(30) Foreign Application Priority Data

Apr. 15, 2020   (CN) .......................... 202010293758.4

(51) Int. Cl.
| | | |
|---|---|---|
| *A61F 13/15* | (2006.01) | |
| *A61F 13/36* | (2006.01) | |
| *B30B 15/06* | (2006.01) | |
| *B30B 15/14* | (2006.01) | |
| *B30B 9/28* | (2006.01) | |

(52) U.S. Cl.
CPC ........ *A61F 13/15707* (2013.01); *A61F 13/36* (2013.01); *B30B 9/28* (2013.01); *B30B 15/062* (2013.01); *B30B 15/14* (2013.01); *A61F 2013/15821* (2013.01)

(58) Field of Classification Search
CPC ................ A61F 13/15707; A61F 13/36; A61F 2013/15821; B30B 15/062; B30B 15/14
See application file for complete search history.

(56) References Cited

FOREIGN PATENT DOCUMENTS

| CN | 104106170 A | 10/2014 |
|---|---|---|
| CN | 104229151 A | 12/2014 |
| CN | 205291669 U | 6/2016 |
| CN | 205553303 U | 9/2016 |
| CN | 205685779 U | 11/2016 |
| CN | 107776168 A | 3/2018 |
| CN | 208197617 U | 12/2018 |
| CN | 208197635 U | 12/2018 |
| CN | 209473742 U | 10/2019 |

*Primary Examiner* — Alma Pipic

(57) ABSTRACT

Provided is a method for manufacturing a medical sponge for orthopedic treatment by unilateral pressing, which relates to compaction of medical sponges. The method includes a pressing machine that includes a bottom bracket, two vertical support rods, a middle support, a U-shaped support, a drive assembly and two film pressing assemblies. The two vertical support rods are fixed vertically on both ends of the bottom bracket, respectively. The middle support is fixedly arranged on a middle of an upper side of the bottom bracket, and the U-shaped support is fixedly arranged on a top of the middle support. The drive assembly is fixedly arranged on the U-shaped support. The two film pressing assemblies are fixedly arranged between two outer sides of the U-shaped support and the two vertical support rods, respectively.

7 Claims, 9 Drawing Sheets

METHOD FOR MANUFACTURING MEDICAL SPONGE FOR ORTHOPEDIC TREATMENT BY UNILATERAL PRESSING

CROSS-REFERENCE TO RELATED APPLICATIONS

This application claims the benefit of priority from Chinese Patent Application No. 202010293758.4, filed on Apr. 15, 2020. The content of the aforementioned application, including any intervening amendments thereto, is incorporated herein by reference in its entirety.

TECHNICAL FIELD

This application relates to compaction of medical sponges, and more particularly to a method for manufacturing a medical sponge for orthopedic treatment by unilateral pressing.

BACKGROUND

Medical collagen sponge is commonly used in surgery, which can act as a filler to quickly stop bleeding, prevent adhesions and accelerate the wound healing. Moreover, it can also reduce postoperative complications, and thus it has been widely used in neurosurgery, orthopedics, gynecology, general surgery, operating room, etc.

With regard to the application in the orthopedic treatment, the medical collagen sponge has an excellent curative effect for various fractures, bone tumors, and bleeding in the intraspinal canal and bone joint operation, and can be rapidly degraded and absorbed in the human body. Moreover, it also plays a role in activating the bone morphogenetic proteins to promote the formation of new bones. The collagen sponge can also be filled in residual cavities with tissue loss, cavities formed after bone nail removal and bone marrow cavities of patients with osteoporosis.

The commercially-available medical sponges all have a flat structure, and the manufacturing process has been disclosed in detail in Chinese Patent Application No. 202010223230X. However, this document still fails to solve the technical problem that how to press a large area of a semi-solidified medical sponge into a flat sponge with less moisture.

SUMMARY

In view of the defects in the prior art, this application provides a method for manufacturing a medical sponge for orthopedic treatment by unilateral pressing, in which a large area of the medical sponge can be compacted.

The technical solutions of this application are described as follows.

This application provides a method for manufacturing a medical sponge for orthopedic treatment by unilateral pressing, wherein a pressing machine is applied in the method:

the pressing machine comprises a bottom bracket, two vertical support rods, a middle support, a U-shaped support, a drive assembly and two film pressing assemblies; the two vertical support rods are fixed vertically on both ends of the bottom bracket, respectively; the middle support is fixedly arranged on a middle of an upper side of the bottom support, and the U-shaped support is fixedly arranged on a top of the middle support; the drive assembly is fixedly arranged on the U-shaped support; the two film pressing assemblies are fixedly arranged between two outer sides of the U-shaped support and the two vertical support rods, respectively; each of the two film pressing assemblies comprises a first transmission shaft, a support of the first transmission shaft, a horizontal spiral bevel gear, a vertical spiral bevel gear, an outer frame, an inner frame, two first rotating shaft seats, four second rotating shaft seats, a first rotating shaft and a second rotating shaft; the four second rotating shaft seats are provided at a middle of an upper end, a middle of a lower end, a middle of a left end and a middle of a right end of the outer frame, respectively; the two first rotating shaft seats are provided at a middle of an upper end and a middle of a lower end of the inner frame, respectively; the two first rotating shaft seats are connected to the two second rotating shaft seats arranged on the upper end and the lower end of the outer frame, respectively, through the first rotating shaft; the two second rotating shaft seats arranged on the left end and the right end of the outer frame are connected to one outer side of the U-shaped support and one of the two vertical support rods, respectively, through the second rotating shaft; the support of the first transmission shaft is fixedly arranged on a top of the second rotating shaft seat;

the first transmission shaft is rotatably arranged in the support of the first transmission shaft; two ends of the first transmission shaft respectively extends out of two sides of the support of the first transmission shaft; one end of the first transmission shaft is connected to a rotation end of the drive assembly, and the other end of the first transmission shaft is connected to the horizontal spiral bevel gear; the vertical spiral bevel gear is coaxially connected to the first rotating shaft connecting the first rotating shaft seat on the upper end of the outer frame with the second rotating shaft seat on the upper end of the inner frame; the vertical spiral bevel gear and the horizontal spiral bevel gear are engaged for transmission; and the method comprises:

adjusting the inner frame and the outer frame to an initial position such that the inner frame, the outer frame and the two vertical support rods are in a same plane, and are perpendicular to a ground; driving, by the drive assembly, the first transmission shaft to rotate, so as to drive the inner frame to rotate in the outer frame through engagement between the vertical spiral bevel gear and the horizontal spiral bevel gear; placing a press plate on a semi-solidified medical sponge block, wherein the press plate is a metal plate with strong mechanical strength; placing the semi-solidified medical sponge block and the press plate horizontally at a bottom of the outer frame, so as to squeeze the press plate with frame rods of the inner frame; keeping a motor operating forward and backward to drive the frame rods of the inner frame to repeatedly squeeze the press plate, so as to repeatedly squeeze two sides of the semi-solidified medical sponge block under the press plate to produce the medical sponge.

In some embodiments, the drive assembly comprises the motor and a second transmission shaft; the motor is fixedly arranged on an upper part of the middle support, and the second transmission shaft is rotatably arranged in the U-shaped support through a bearing seat; the motor is connected to the second transmission shaft through a first transmission assembly, and two ends of the second transmission shaft are respectively connected to two first transmission shafts through a transmission pair.

In some embodiments, the first transmission assembly comprises a first transmission gear, a first gear transmission belt and a second transmission gear; the first transmission gear is fixedly arranged at a driving end of the motor, and the second transmission gear is coaxially and fixedly connected to the second transmission shaft; the first gear transmission belt is provided on the first transmission gear and the second transmission gear.

In some embodiments, the transmission pair comprises a third transmission gear, a second gear transmission belt, a fourth transmission gear, a fifth transmission gear, a third gear transmission belt and a sixth transmission gear; the third transmission gear is coaxially and fixedly connected to one end of the second transmission shaft; the fourth transmission gear is coaxially and fixedly connected to the fifth transmission gear; a transmission gear shaft is provided between the fourth transmission gear and the fifth transmission gear and is fixedly arranged on a side of the U-shaped support, and an outer end of the transmission gear shaft is fixedly connected to the second rotating shaft; the second gear transmission belt is provided on the third transmission gear and the fourth transmission gear; the third gear transmission belt is provided on the fifth transmission gear and the sixth transmission gear; and the sixth transmission gear is coaxially and fixedly connected to one end of the first transmission shaft;

when the press machine is in operation, the motor drives the first transmission gear to rotate, so as to drive the second transmission gear to rotate through the first gear transmission belt; the second transmission shaft drives the transmission pair to operate; through sequential transmission of the second gear transmission belt and the third gear transmission belt, the sixth transmission gear is driven to rotate, so as to drive the first transmission shaft to rotate, thereby driving the corresponding film pressing assembly to work.

In some embodiments, the inner frame is a rectangular frame, and a horizontal length of the inner frame is greater than a vertical width of the outer frame.

In some embodiments, each of the frame rods of the inner frame has a curved side surface.

In some embodiments, upper and lower frame rods of the inner frame are connected through a plurality of connecting rods.

In the method provided herein, the motor drives the first transmission gear to rotate, so as to drive the second transmission gear to rotate through the first transmission gear. Then the second transmission shaft drives the two transmission pairs to operate, so as to drive the two first transmission shafts of the two film pressing assemblies to rotate. Through the engagement between the vertical spiral bevel gear and the horizontal spiral bevel gear, the rotation of the first transmission shaft drives the inner frame to rotate in the outer frame, so as to squeeze the press plate through the frame rods of the inner frame, enabling the compaction of the semi-solidified medical sponge.

The pressing machine provided herein can be applied in two different methods. A medical collagen sponge block can be pressed unilaterally or bilaterally, and the pressing mode can be adjusted according to the requirements of density and pressing force. Moreover, the two pressing modes can also be used in sequence, which has extremely high operation flexibility without the need to modify the equipment.

Figure 1:
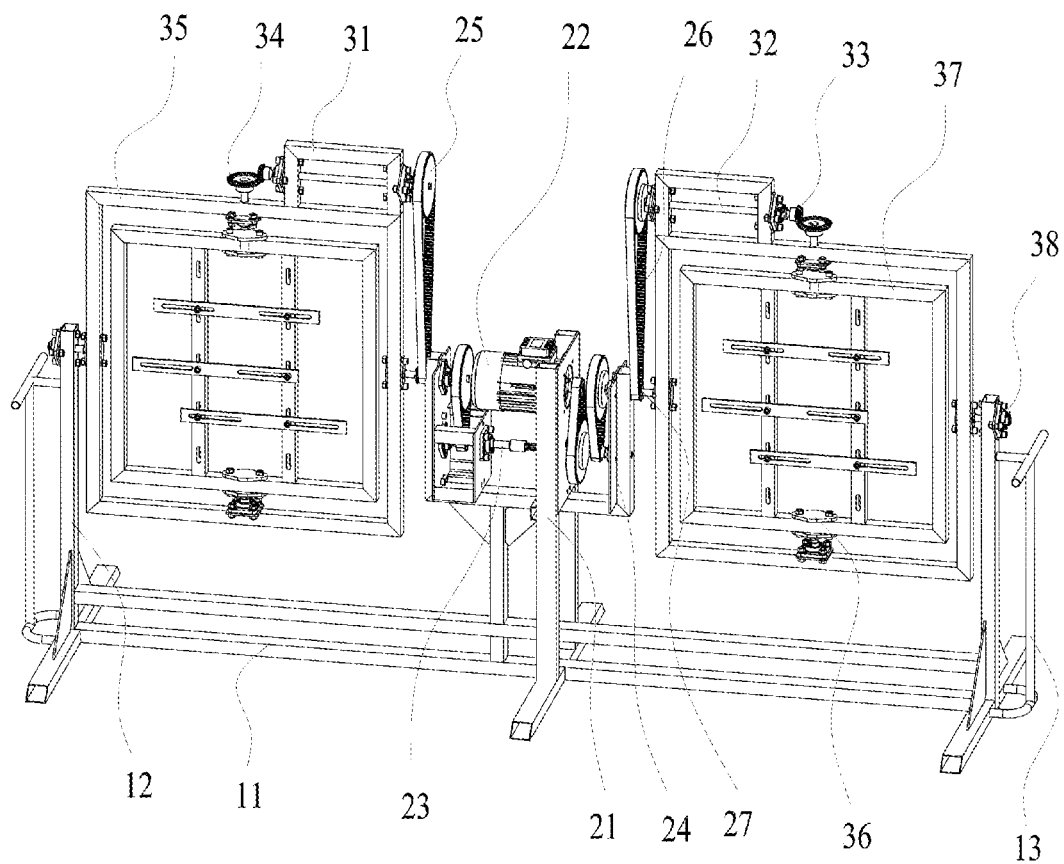
FIG. 1 is a perspective view of a structure of a pressing machine according to an embodiment of the present disclosure.

In the drawings, 11—bottom bracket; 12—vertical support rod; 13—lifting rod; 21—middle support; 22—motor; 23—second transmission shaft; 24—U-shaped support; 25—sixth transmission gear; 26—third gear transmission belt; 27—fifth transmission gear; 28—fourth transmission gear; 29—second gear transmission belt; 210—third transmission gear; 211—second transmission gear; 212—first gear transmission belt; 213—first transmission gear; 31—support of a first transmission shaft; 32—first transmission shaft; 33—horizontal spiral bevel gear; 34—vertical spiral bevel gear; 35—outer frame; 36—first rotating shaft seat; 37—inner frame; 38—second rotating shaft seat; 39—first rotating shaft; 51—press plate; 52—top surface of press plate before pressing; 53—top surface of press plate after pressing; 6—medical sponge block; and 71—working trajectory of inner frame.

DETAILED DESCRIPTION OF EMBODIMENTS

In order to render the objects, technical solutions and beneficial effects of the disclosure clearer, the disclosure will be described below in detail in conjunction with accompanying drawings and embodiments. It should be understood that these embodiments are merely illustrative of the disclosure, and are not intended to limit the disclosure.

The operation principles of a drive assembly of the disclosure are described as follows.

As shown in FIGS. 1-5, the drive assembly includes the motor 22 and a second transmission shaft 23. The motor 22 is fixedly arranged on an upper part of the middle support 21. The second transmission shaft 23 is rotatably arranged in the U-shaped support 24 through a bearing seat. The motor 22 is connected to the second transmission shaft 23 through the first transmission assembly, and two ends of the second transmission shaft 23 are respectively connected to two first transmission shafts 32 through a transmission pair. The first transmission assembly includes a first transmission gear 213, a first gear transmission belt 212 and a second transmission gear 211. The first transmission gear 213 is fixedly arranged on a driving end of the motor 22, and the second transmission gear 211 is coaxially connected to the second transmission shaft 32. The first gear transmission belt 212 is provided on the first transmission gear 213 and the second transmission gear 211. The transmission pair includes a third transmission gear 210, a second gear transmission belt 29, a fourth transmission gear 28, a fifth transmission gear 27, a third gear transmission belt 26 and a sixth transmission gear 25. The third transmission gear 210 is coaxially and fixedly connected to an end of the second transmission shaft 32. The fourth transmission gear 28 and the fifth transmission gear 27 are coaxially and fixedly connected, and the transmission gear shaft between the fourth transmission gear 28 and the fifth transmission gear 27 is fixedly arranged on one side of the U-shaped support 24. The outer end of the transmission gear shaft between the fourth transmission gear 28 and the fifth transmission gear 27 is also fixedly connected to a frame rotating shaft. The second gear transmission belt 29 is provided on the third transmission gear 210 and the fourth transmission gear 28. The third gear transmission belt 26 is provided on the fifth transmission gear 27 and the sixth transmission gear 25. The sixth transmission gear 25 is coaxially and fixedly connected to one end of the first transmission shaft 32. The inner frame 37 is a rectangular frame, and the horizontal length of the inner frame 37 is greater than the vertical width of the outer frame 35.

When the drive assembly is in operation, the motor 22 drives the first transmission gear 213 to rotate, so as to drive the second transmission gear 32 to rotate through the first gear transmission belt 212. The second transmission shaft 32 drives the transmission pair to operate; through sequentially transmission of the second gear transmission belt 29 and the third gear transmission belt 26, the sixth transmission gear is driven to rotate, so as to drive the first transmission shaft 23 to rotate, thereby driving the corresponding film pressing assembly to work.

Embodiment 1

The working mode of the inner frame is described as follows. As shown in the perspective view of a structure of the pressing machine in FIG. 1 and the front view of the pressing machine in FIG. 2, the pressing machine includes a bottom bracket 11, two vertical support rods 12, a middle support 21, a U-shaped support 24, a drive assembly, a film pressing assembly and a lifting rod 13. The two vertical support rods 12 are provided and fixed vertically on both ends of the bottom bracket 11, respectively. The middle support 21 is fixedly arranged on a center of an upper end of the bottom bracket 11, and the U-shaped support 24 is fixedly arranged on a top of the middle support 21. The drive assembly is fixedly arranged on the U-shaped support 24. Two film pressing assemblies with same structure are provided and fixedly arranged between two outer sides of the U-shaped support 24 and the two vertical support rods 12, respectively.

Figure 3:
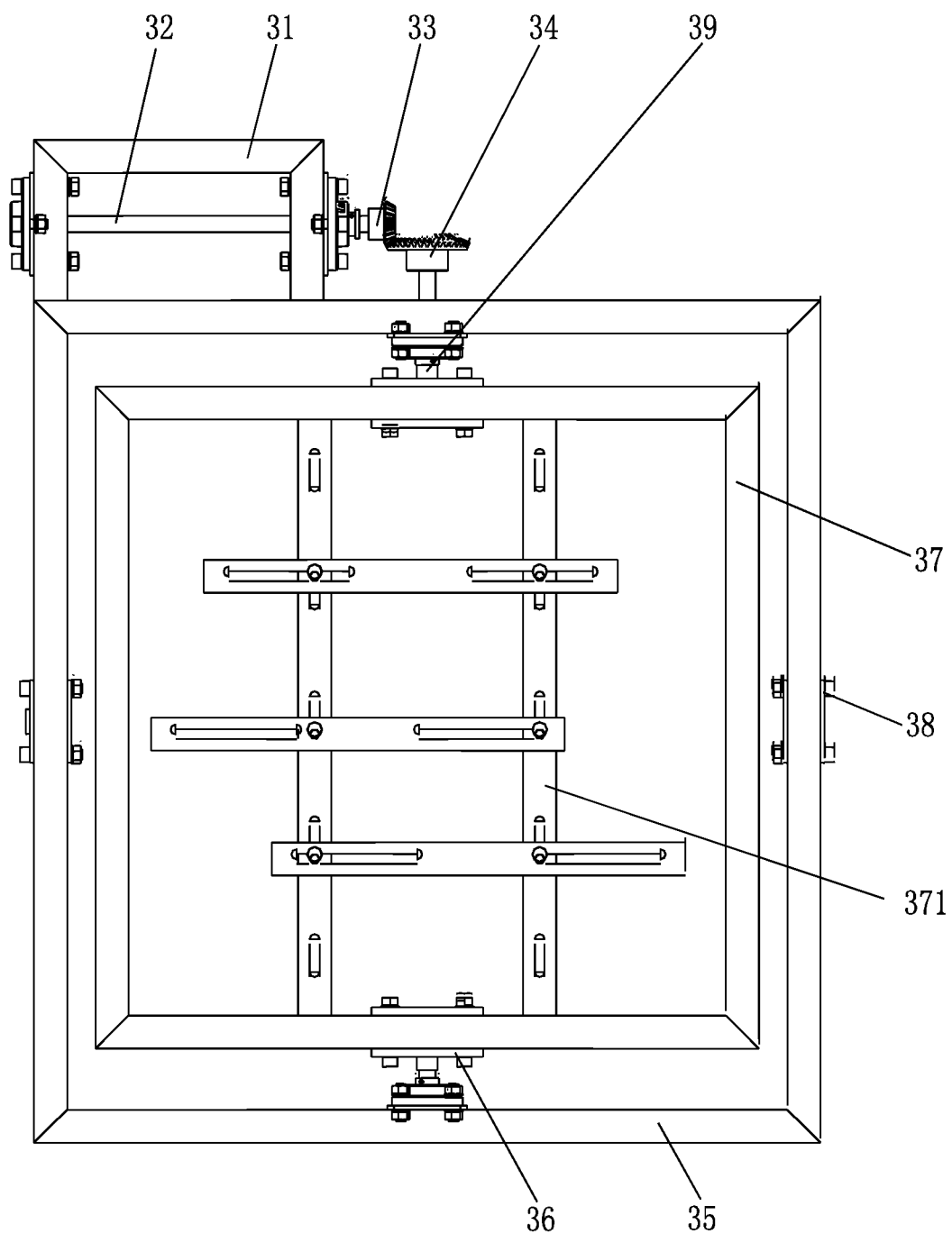
FIG. 3 is a front view of a film pressing assembly according to an embodiment of the present disclosure.
Figure 4:
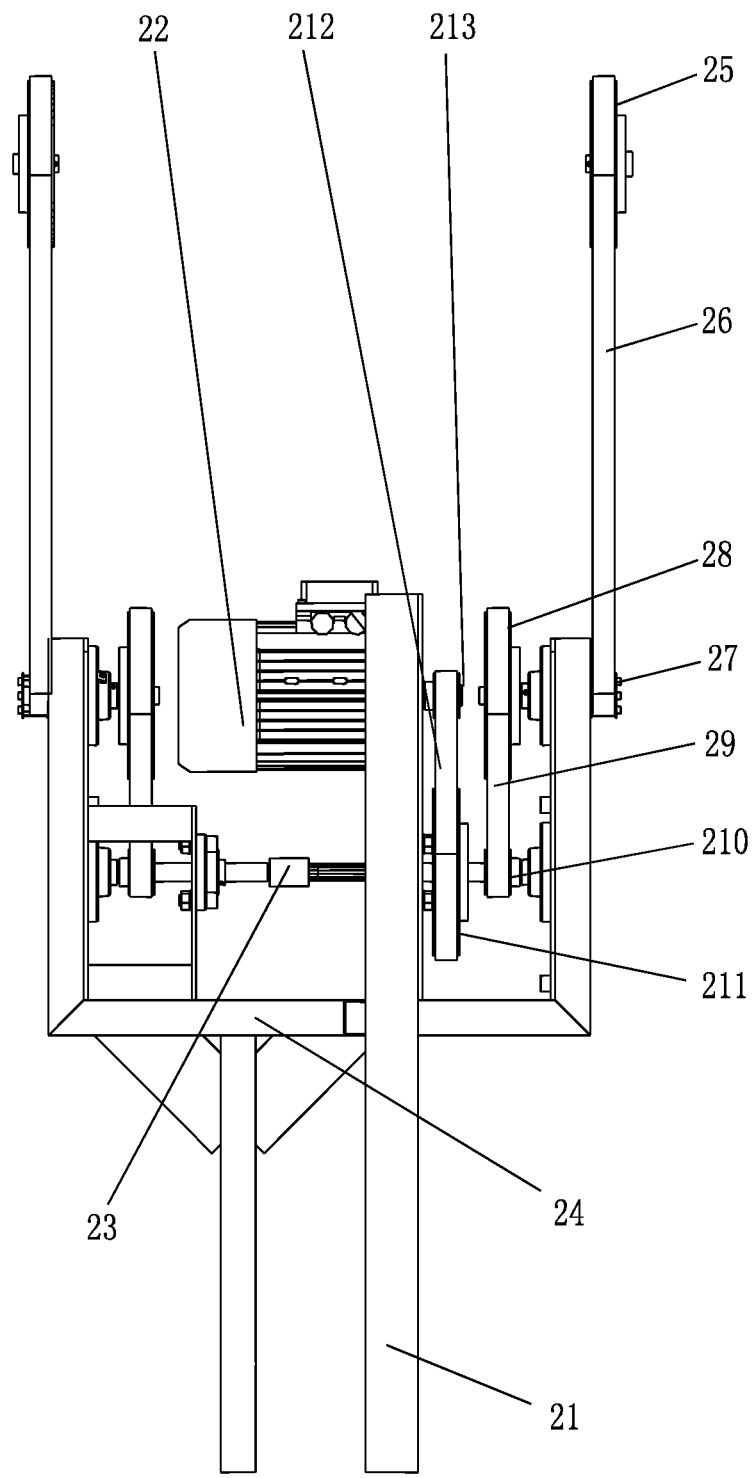
FIG. 4 is a front view of a drive assembly according to an embodiment of the present disclosure.
Figure 5:
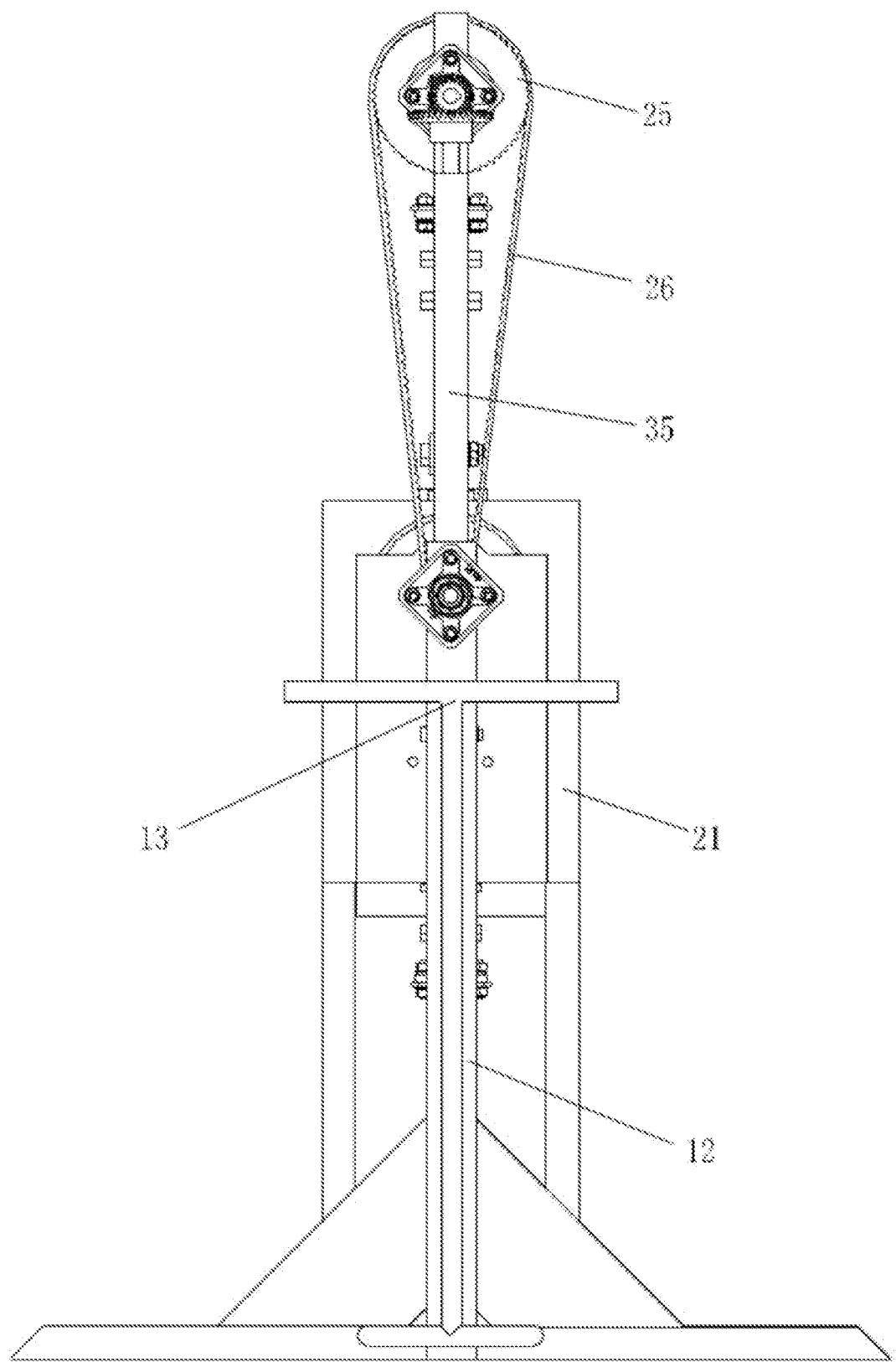
FIG. 5 is a left side view of the pressing machine according to an embodiment of the present disclosure.

As shown in the front view of the film pressing assembly in FIG. 3, each film pressing assembly includes a support of a first transmission shaft 31, a first transmission shaft 32, a horizontal spiral bevel gear 33, a vertical spiral bevel gear 34, an outer frame 35, a first rotating shaft seat 36, an inner frame 37, an second rotating shaft seat 38, a first rotating shaft 39 and a second rotating shaft. A center of an upper end, a center of a lower end, a center of a left end and a center of a right end of the outer frame 35 are respectively provided with the second rotating shaft seat 38. A center of an upper end and a center of a lower end of the inner frame 37 are respectively provided with the first rotating shaft seat 36. The two first rotating shaft seats 36 are connected to the two second rotating shaft seats 38 arranged on the upper end and the lower end of the outer frame, respectively, through the first rotating shaft 39. The two second rotating shaft seats 38 arranged on the left end and the right end of the outer frame 35 are connected to one outer side of the U-shaped support 24 and one of the two vertical support rods 12 through the second rotating shaft. The second transmission shaft support 31 is fixedly arranged on a top of the second rotating shaft seat 38, and the first transmission shaft 32 is rotatably arranged in the second transmission shaft support 31. Two ends of the first transmission shaft 32 respectively extend to two outer sides of the second transmission shaft support 31. One end of the first transmission shaft 32 is connected to a rotatable end of the drive assembly, and the other end of the first transmission shaft 32 is connected to the horizontal spiral bevel gear 33. The vertical spiral bevel gear 34 is coaxially connected to the first rotating shaft 39 in the second rotating shaft seat 38 arranged at an upper end of the outer frame 35. The vertical spiral bevel gear 34 and the horizontal spiral bevel gear 33 are engaged through the gear to drive.

The drive assembly drives the first transmission shaft 32 to rotate, then to drive the horizontal spiral bevel gear 33 coaxial with the first transmission shaft 32 to rotate. Through the engagement between the vertical spiral bevel gear 34 and the horizontal spiral bevel gear 33, the rotation of the first transmission shaft 32 drives the inner frame 37 to rotate in the outer frame 35, so as to squeeze the press plate through the frame rods of the inner frame, enabling the compaction of the semi-solidified medical sponge. The frame rod of the inner frame 37 is an arc-shaped rod, so that the contact area of the frame rod of the inner frame 37 is larger when it comes into contact with the object to be compacted. In order to enhance the mechanical strength, frame rods of the inner frames 37 are also connected by several connecting rods.

To further illustrate the disclosure, in this embodiment, the pressing machine is configured to compact the medical sponge in the semi-solidified state (hereinafter referred to as the semi-solidified state), so as to further elaborate the method for manufacturing a medical sponge for orthopedic treatment by unilateral pressing. As shown in a top view of the film pressing assembly when rotating to a limit position (the working position is around the limit position) in FIG. 6 and the schematic diagram of a pressing machine used to squeeze the medical sponge in FIG. 7.

Figure 2:
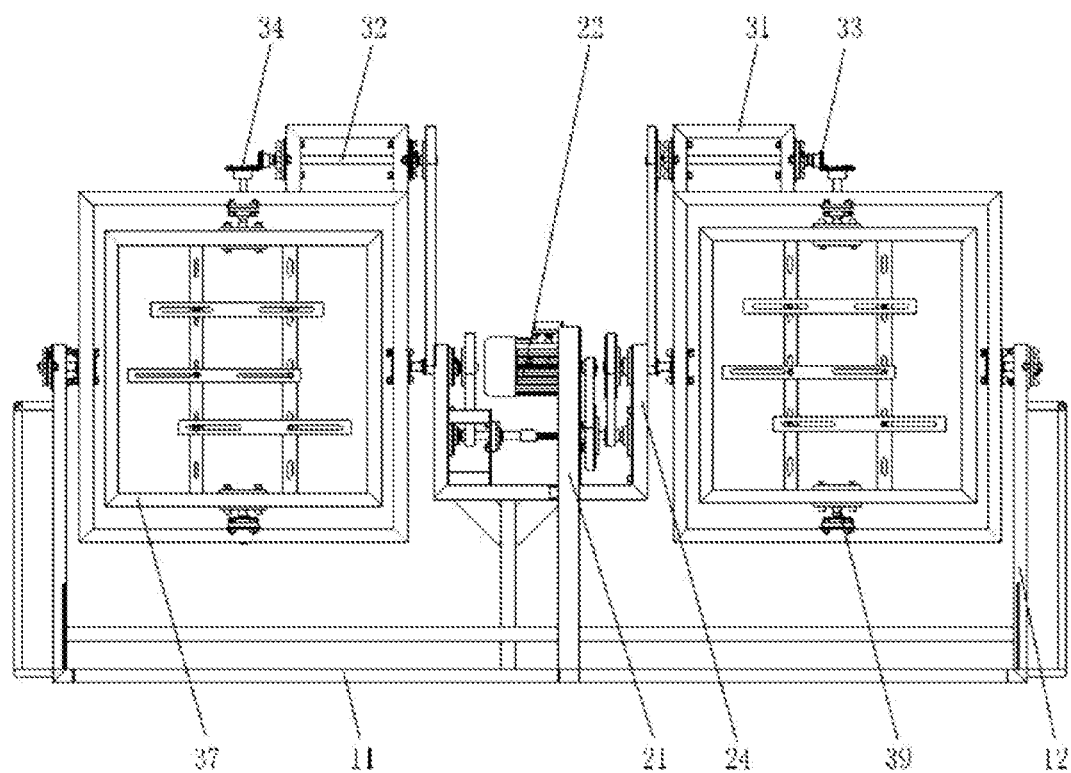
FIG. 2 is a front view of the pressing machine according to an embodiment of the present disclosure, where the pressing machine is in an initial state according to Embodiment 1, and an inner frame, an outer frame and vertical support rods are all in the same plane and perpendicular to the ground.
Figure 7:
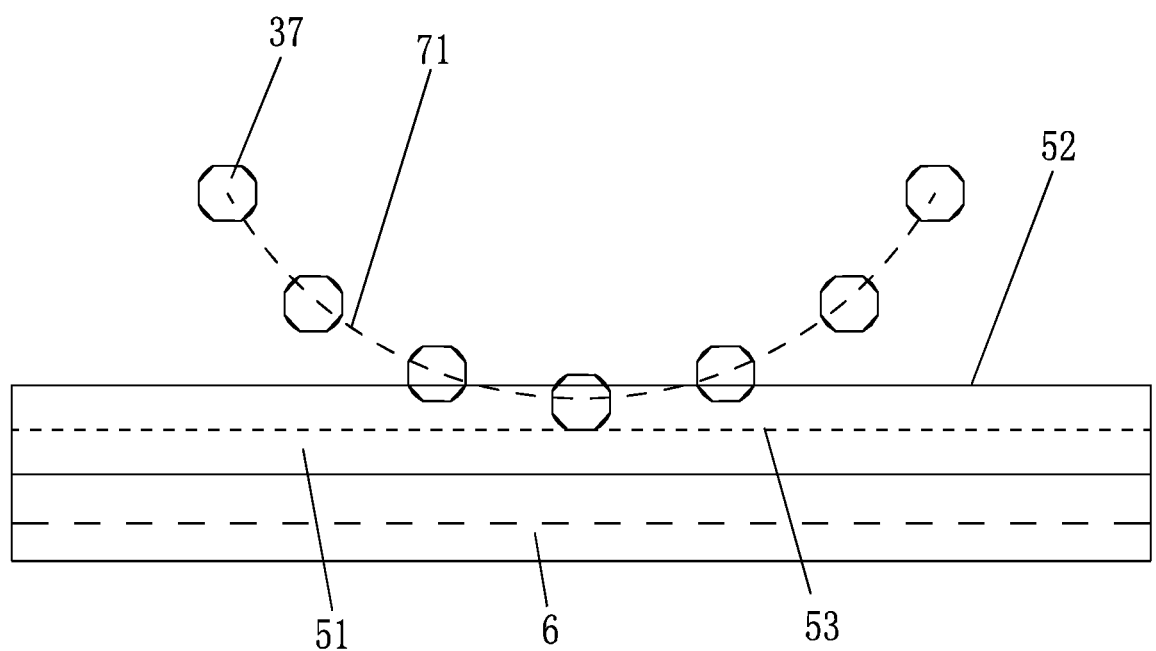
FIG. 7 schematically illustrates a working trajectory of the inner frame when the film pressing assembly of the pressing machine is rotated to the working position according to Embodiment 1 of the present disclosure, where the working trajectory only illustrates the movement direction of the inner frame, and the inner frame will not follow a complete trajectory.

When the pressing machine is in operation, the inner frame 37 and the outer frame 35 are adjusted to the initial position, as shown in FIG. 2, such that the inner frame 37, the outer frame 35 and the two vertical support rods 12 are in a same plane, and are perpendicular to a ground. The drive assembly drives the first transmission shaft 32 to rotate, so as to drive the inner frame 37 to rotate in the outer frame 35 through engagement between the vertical spiral bevel gear 34 and the horizontal spiral bevel gear 33. The movement of the inner frame 37 is shown in the trace 71. A press plate 51 is place on the upper end of the semi-solidified medical sponge 6. The press plate 51 is preferably a metal plate such as a steel plate with high mechanical strength. The medical sponge 6 and the press plate 51 are placed horizontally at the bottom of the outer frame 35. Before compaction, the upper surface of the press plate 51 is shown as the top surface of the press plate before pressing 52. The press plate 51 is pressed by the frame rod of the inner frame 37. One edging of the inner frame 37 works along the counterclockwise direction of the track 71 as shown in FIG. 7 when the motor is operating forward. The other edging of the inner frame 37 works along the clockwise direction of the track 71 as shown in FIG. 7 when the motor is operating backward. The motor is operated forward and backward to drive the frame rod of the inner frame 37 to repeatedly squeeze the press plate 51, so as to repeatedly squeeze two sides of the semi-solidified medical sponge block under the press plate to produce the medical sponge.

The medical sponge 6 will be compacted and deformed after squeezing, and the upper surface of the press plate 51 will drop. The upper surface of the press plate 51 is shown as the top surface of the press plate after pressing 53, so as to realize the compaction of the medical sponge.

Embodiment 2

Figure 6:
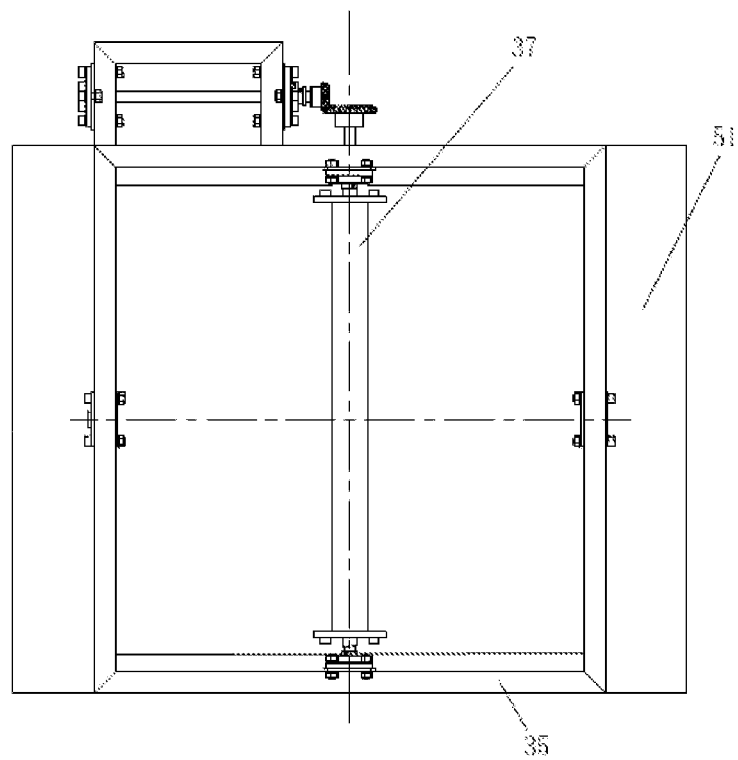
FIG. 6 is a top view of the film pressing assembly when rotating to a limit position (the working position is around the limit position) according to Embodiment 1 of the present disclosure, where the outer frame is parallel to the ground, and the inner frame is perpendicular to the ground.
Figure 9:
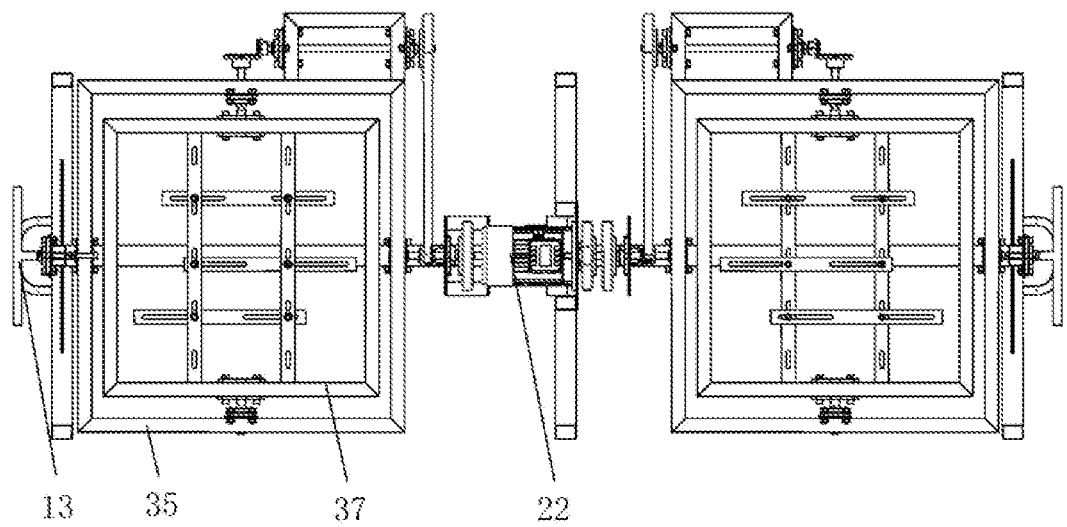
FIG. 9 is a top view of the pressing machine according to Embodiment 2 of the present disclosure in a working position, where the outer frame and the inner frame are in the same plane, and both of the outer frame and the inner frame are parallel to the ground.

This pressing machine actually has another working mode, that is, both the inner frame 37 and outer frame 35 work (bilateral) at the same time. As shown in FIGS. 6 and 9, in the initial working state, the outer frame 35 is perpendicular to the inner frame 37, and the outer frame 35 and the inner frame 37 are perpendicular to the ground. When the motor 22 is in operation, the outer frame 35 and the inner frame 37 are respectively turned 90° under the drive of the transmission mechanism.

Figure 8:
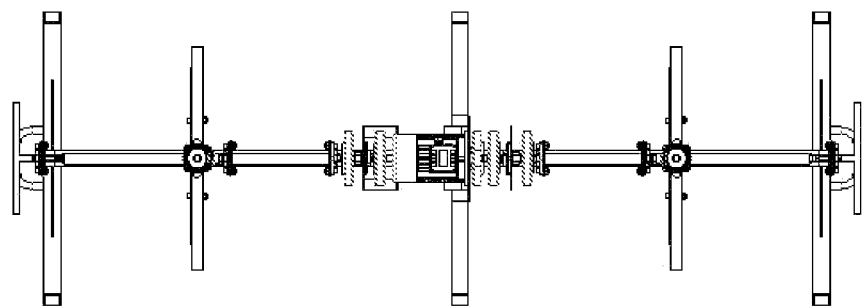
FIG. 8 is a top view of the pressing machine according to Embodiment 2 of the present disclosure in an initial position, where the outer frame and the inner frame are perpendicular to each other, and both of the outer frame and the inner frame are perpendicular to the ground.

As shown in FIGS. 7 and 8, the outer frame 35 and the inner frame 37 will gradually move to a state parallel to the ground, such that the outer frame 35 and the inner frame 37 are on a same plane. The outer frame 35 and the inner frame 37 are both parallel to the ground and perpendicular to the vertical support rod 12.

Figure 10:
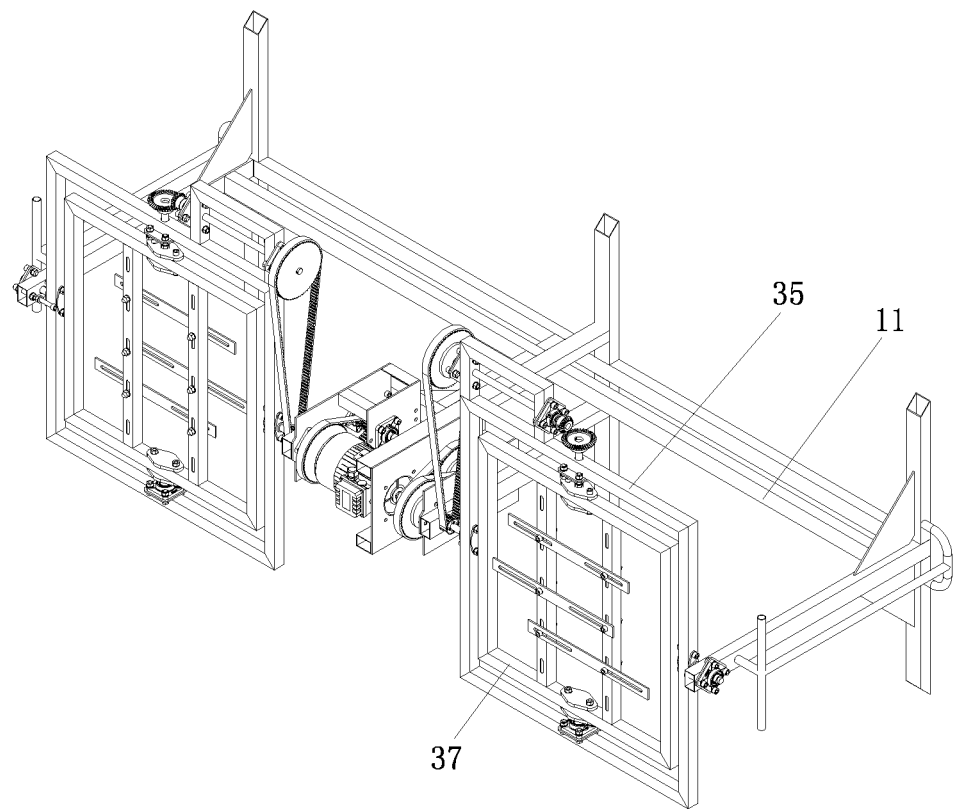
FIG. 10 is a perspective view of the pressing machine according to Embodiment 2 of the present disclosure in the working position.
Figure 11:
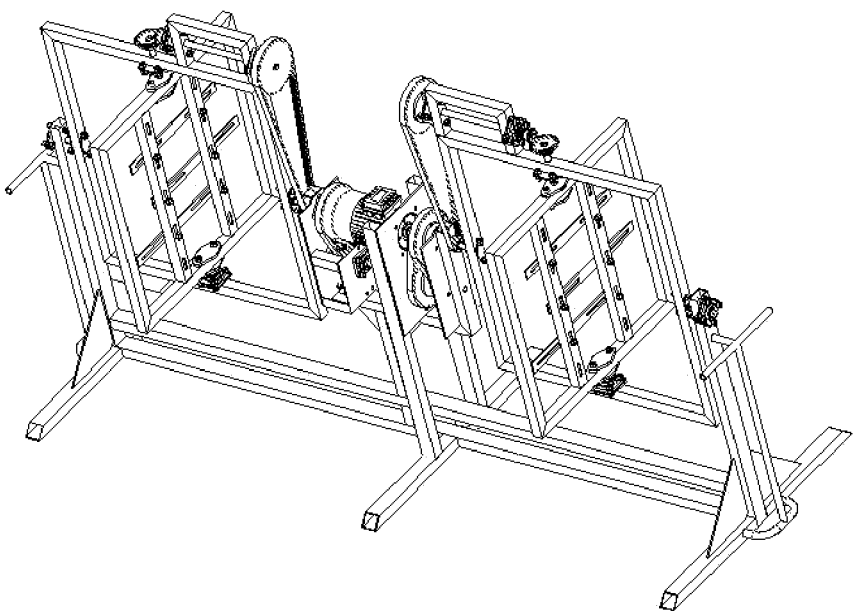
FIG. 11 is a perspective view of the pressing machine according to Embodiment 2 of the present disclosure in the initial position.
Figure 12:
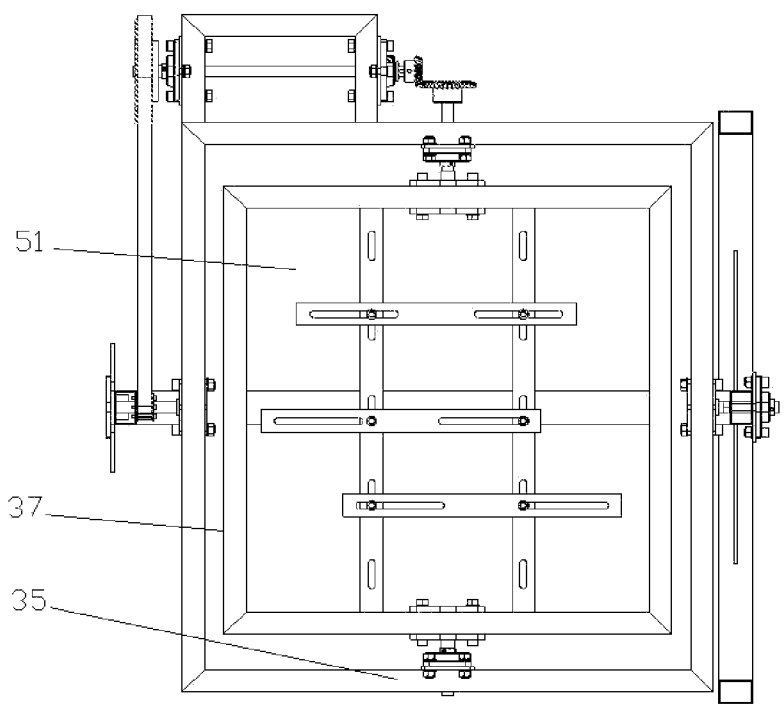
FIG. 12 schematically shows a contact between the outer frame and the inner frame and a bottom medical sponge in the working position according to Embodiment 2.
Figure 13:
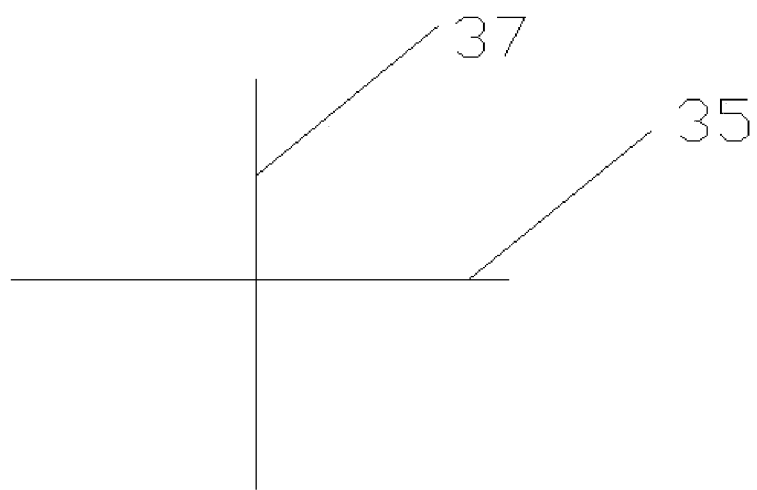
FIG. 13 is a front view of the inner frame and the outer frame when the film pressing assembly is rotated to the working position according to Embodiment 1 of the present disclosure, where the inner frame and the outer frame are perpendicular to each other; and the outer frame is parallel to the ground, and the inner frame is perpendicular to the ground.

As shown in FIG. 10, the press plate 51 (the shape of the press plate 51 is smaller than or equal to the outer frame 35, and larger than or equal to the inner frame 37) and the medical sponge to be pressed placed under the press plate 51 are pushed below the outer frame 35 and the inner frame 37. Continuing to turn on the motor 22, the left frame rod of the inner frame 37 and the bottom frame rod of the outer frame 35 (or the right frame rod of the inner frame 37 and the top frame rod of the outer frame 35) continue to flip down, so as to contact the press plate 51, respectively. At this time, the press plate 51 is parallel to the horizontal frame. When the motor 22 operates forward, the left frame rod of the inner frame 37 and the top frame rod of the outer frame 35 squeeze one corner and two sides of the press plate 51, and when the motor 22 rotates backward, the right frame rod of the inner frame 37 and the bottom frame rod of the outer frame 35 squeeze the other corner and the other two sides of the press plate 51. The motor keeps operating forward and backward, and the four frame rods of the inner frame 37 and the outer frame 35 repeatedly squeeze the four sides of the press plate 51, so as to repeatedly squeeze the medical sponge under the press plate 51 to produce the medical sponge.

Embodiment 3

The sponge is first pressed roughly according to its thickness, and is quickly pressed to the specified thickness using the unilateral working mode in Embodiment 1. And then the four corners of the sponge are pressed to the specified thickness using the bilateral working mode in Embodiment 2.

Two different working methods can be derived from a same structure of this disclosure, which can perform unilateral press or bilateral press to the medical collagen sponge placed under the press plate, respectively.

In the case of unilateral pressing, the compaction speed is relatively fast, but the surface of the sponge is uneven. In the case of bilateral pressing, the two vertical edges of a corner are pressed, and the pressed surface of the sponge is relatively flat. However, since the pressure is applied to the corners, the compaction speed of sponge is relatively slow. Therefore, the two working methods have their own advantages and disadvantages.

Therefore, an appropriate working mode can be selected according to the actual requirements of density of the sponge sheet, pressing force and compaction speed. If a fast pressing process is needed, the unilateral method is preferable, and if the flat upper surface is needed, the bilateral pressing can be adopted. The two working methods can also be applied in sequence, specifically, the sponge is first pressed to the specified thickness by unilateral pressing method, and then adjusted to flat by the bilateral pressing method. When the two working methods are exchanged, there is no need to adjust the equipment, only need to debug to a different initial position. Therefore, this equipment has very high working flexibility, and different working modes can be achieved without modification of the equipment, and the process adjustment is very flexible.

The objects, technical solutions and beneficial effects of the invention are described clearly with reference to the accompanying embodiments. It should be understood that these embodiments are merely illustrative of the disclosure, and are not intended to limit the disclosure. Any changes, equivalent modifications and improvements made by those skilled in the art without departing from the spirit of the present disclosure shall fall within the scope of the present disclosure.

What is claimed is:

1. A method for manufacturing a medical sponge for orthopedic treatment by unilateral pressing, wherein a pressing machine is applied in the method:

the pressing machine comprises a bottom bracket, two vertical support rods, a middle support, a U-shaped support, a drive assembly and two film pressing assemblies; one of the two vertical support rods is fixed vertically on one end of the bottom bracket; the other one of the two vertical support rods is fixed vertically on the other end of the bottom bracket; the middle support is fixedly arranged on a middle of an upper side of the bottom bracket, and the U-shaped support is fixedly arranged on a top of the middle support; the drive assembly is fixedly arranged on the U-shaped support; one of the two film pressing assemblies is fixedly arranged between one of two outer sides of the U-shaped support and one of the two vertical support rods; the other one of the two film pressing assemblies is fixedly arranged between the other one of the two outer sides of the U-shaped support and the other one of the two vertical support rods; each of the two film pressing assemblies comprises a first transmission shaft, a support of the first transmission shaft, a horizontal spiral bevel gear, a vertical spiral bevel gear, an outer frame, an inner frame, two first rotating shaft seats, four second rotating shaft seats, a first rotating shaft and a second rotating shaft; each of the four second rotating shaft seats is provided at a middle of an upper end, a middle of a lower end, a middle of a left end and a middle of a right end of the outer frame, respectively; each of the two first rotating shaft seats is provided at a middle of an upper end and a middle of a lower end of the inner frame, respectively; each of the two first rotating shaft seats is connected to two of the four second rotating shaft seats arranged on the upper end and the lower end of the outer frame, respectively, through the first rotating shaft; two of the four second rotating shaft seats arranged on the left end and the right end of the outer frame are connected to one outer side of the U-shaped support and one of the two vertical support rods, respectively, through the second rotating shaft; the support of the first transmission shaft is fixedly arranged on a top of one of the four second rotating shaft seats; the first transmission shaft is rotatably arranged in the support of the first transmission shaft; one of two ends of the first transmission shaft extends out of one of two sides of the support of the first transmission shaft; the other one of the two ends of the first transmission shaft extends out of the other one of the two sides of the support of the first transmission shaft; one end of the first transmission shaft is connected to a rotation end of the drive assembly, and the other end of the first transmission shaft is connected to the horizontal spiral bevel gear; the vertical spiral bevel gear is coaxially connected to the first rotating shaft connecting the first rotating shaft seat on the upper end of the outer frame with one of the four second rotating shaft seats on the upper end of the inner frame; and the vertical spiral bevel gear and the horizontal spiral bevel gear are engaged for transmission; and the method comprises:

adjusting the inner frame and the outer frame to an initial position such that the inner frame, the outer frame and the two vertical support rods are in a same plane, and are perpendicular to a ground; driving, by the drive assembly, the first transmission shaft to rotate, so as to drive the inner frame to rotate in the outer frame through engagement between the vertical spiral bevel gear and the horizontal spiral bevel gear; placing a press plate on a semi-solidified medical sponge block, wherein the press plate is a metal plate; placing the semi-solidified medical sponge block and the press plate horizontally at a bottom of the outer frame, so as to squeeze the press plate with frame rods of the inner frame; and keeping a motor operating forward and backward to drive the frame rods of the inner frame to repeatedly squeeze the press plate, so as to repeatedly squeeze two sides of the semi-solidified medical sponge block under the press plate to produce the medical sponge.

2. The method of claim 1, wherein the drive assembly comprises the motor and a second transmission shaft; the motor is fixedly arranged on an upper part of the middle support, and the second transmission shaft is rotatably arranged in the U-shaped support through a bearing seat; and the motor is connected to the second transmission shaft through a first transmission assembly, and each of two ends of the second transmission shaft is connected to the first transmission shaft through a transmission pair.

3. The method of claim 2, wherein the first transmission assembly comprises a first transmission gear, a first gear transmission belt, and a second transmission gear; the first transmission gear is fixedly arranged at a driving end of the motor, and the second transmission gear is coaxially and fixedly connected to the second transmission shaft; and the first gear transmission belt is provided on the first transmission gear and the second transmission gear.

4. The method of claim 2, wherein the transmission pair comprises a third transmission gear, a second gear transmission belt, a fourth transmission gear, a fifth transmission gear, a third gear transmission belt and a sixth transmission gear; the third transmission gear is coaxially and fixedly connected to one end of the second transmission shaft; the fourth transmission gear is coaxially and fixedly connected to the fifth transmission gear; a transmission gear shaft is provided between the fourth transmission gear and the fifth transmission gear and is fixedly arranged on a side of the U-shaped support, and an outer end of the transmission gear shaft is fixedly connected to the second rotating shaft; the second gear transmission belt is provided on the third transmission gear and the fourth transmission gear; the third gear transmission belt is provided on the fifth transmission gear and the sixth transmission gear; and the sixth transmission gear is coaxially and fixedly connected to one end of the first transmission shaft;

when the pressing machine is in operation, the motor drives the first transmission gear to rotate, so as to drive the second transmission gear to rotate through the first gear transmission belt; the second transmission shaft drives the two transmission pairs to operate; and through sequentially transmission of the second gear transmission belt and the third gear transmission belt, the sixth transmission gear is driven to rotate, so as to drive the first transmission shaft to rotate, thereby driving the two film pressing assemblies to work.

5. The method of claim 4, wherein the inner frame is a rectangular frame, and a horizontal length of the inner frame is greater than a vertical width of the outer frame.

6. The method of claim 5, wherein each of the frame rods of the inner frame has a curved side surface.

7. The method of claim 6, wherein lower and upper frame rods of the inner frame are connected through a plurality of connecting rods.

* * * * *